(12) United States Patent
Guasti

(10) Patent No.: US 8,617,618 B2
(45) Date of Patent: Dec. 31, 2013

(54) TOPICAL COMPOSITIONS CONTAINING MAGALDRATE

(75) Inventor: Pier Luigi Guasti, Dogana (SM)

(73) Assignee: Difass International S.R.L., Prato (IT)

( * ) Notice: Subject to any disclaimer, the term of this patent is extended or adjusted under 35 U.S.C. 154(b) by 153 days.

(21) Appl. No.: 12/593,299

(22) PCT Filed: Mar. 28, 2008

(86) PCT No.: PCT/IB2008/002047
§ 371 (c)(1),
(2), (4) Date: Dec. 29, 2009

(87) PCT Pub. No.: WO2008/142569
PCT Pub. Date: Nov. 27, 2008

(65) Prior Publication Data
US 2010/0092577 A1    Apr. 15, 2010

(30) Foreign Application Priority Data
Mar. 29, 2007 (IT) ............... MI2007A0644

(51) Int. Cl.
*A61K 33/38* (2006.01)
*A61K 33/06* (2006.01)
*A61K 33/30* (2006.01)
*A61K 33/08* (2006.01)

(52) U.S. Cl.
USPC ........... 424/682; 424/642; 424/690; 424/692; 424/618

(58) Field of Classification Search
None
See application file for complete search history.

(56) References Cited

FOREIGN PATENT DOCUMENTS

| EP | 0178895 | A2 | 4/1986 |
| EP | 0220849 | A1 | 5/1987 |
| WO | WO 2006103702 | A2 * | 10/2006 |

* cited by examiner

*Primary Examiner* — David J Blanchard
*Assistant Examiner* — Garen Gotfredson
(74) *Attorney, Agent, or Firm* — Porzio, Bromberg & Newman, P.C.

(57) ABSTRACT

Disclosed are topical compositions containing the active ingredient magaldrate mixed with suitable vehicles and excipients.

4 Claims, No Drawings

TOPICAL COMPOSITIONS CONTAINING MAGALDRATE

CROSS REFERENCE TO RELATED APPLICATION

This is a National Stage of International Application PCT/M2008/002047, filed 28 Mar. 2008, which claims the benefit of Application No. MI2007A644, filed in Italy on 29 Mar. 2007, the disclosures of which Applications are incorporated by reference herein.

This invention relates to topical compositions containing magaldrate which are useful to regenerate skin tissue in the treatment of some diseases of the skin and the nasal, vaginal and rectal mucous membranes. In particular, the compositions according to the invention are useful in the treatment and prophylaxis of irritative and inflammatory states of the skin, and as wound-healing agents.

BACKGROUND TO THE INVENTION

Magaldrate is a substance deriving from the combination of aluminium hydroxide and magnesium hydroxide, corresponding to the formula $Al_5 Mg_{10} (OH)_{31} (SO_4)_2 \cdot xH_2O$, with a molecular weight of approx. 1097. Magaldrate is described as a white, crystalline powder insoluble in water and alcohol; the dry base contains 34-46% magnesium oxide, 21-30% aluminium oxide and 13.3-17.5% sulphur trioxide.

Magaldrate is described in the official monographs of the European Pharmacopoeia (5th edition) and the US Pharmacopoeia (USP 29th edition).

Magaldrate is known and widely used as an ulcer treatment drug, as it possesses marked activity as an antacid buffer. It has been demonstrated that magaldrate has a rapid, persistent ability to maintain the gastric pH in a range of 3-5, and possesses cytoprotective activity. Its efficacy in promoting the healing of gastric and duodenal ulcers is well documented; basically, magaldrate neutralises the gastric acids by inhibiting the proteolytic activity of pepsin. The most recent studies demonstrate that antacids play a more important therapeutic role than as mere palliatives in the treatment of gastric ulcers. Another considerable advantage in the use of magaldrate is its excellent tolerability, demonstrated during its use in gastric disorders: in toxicity tests relating to single and repeated oral doses, it proved almost non-toxic.

Antacid compounds which exert a neutralising effect (US2003157195) or a buffer effect (U.S. Pat. No. 5,362,488 and U.S. Pat. No. 5,436,007) on damaged skin have been described.

Magaldrate not only acts as a pH buffer but possesses cytoprotective activity; published studies demonstrate that this activity is due to protection of the mucosa from lipid peroxidation and the ability to stimulate endogenous prostaglandin ($PGE_2$) synthesis (*Indian J. Physiol Pharmacol.* 2000 July; 44(3):350-4 *Arzneimittelforschung.* 1989 July; 39(7): 786-9); *Hepato-Gastroenterology* 1998; 45:2443-2446).

Evidence in favour of the cytoprotective activity of magaldrate has been obtained in laboratory animals and in tests on humans; it also possesses a marked ability to adsorb lysolecithin and bile acids, and consequently to prevent the epithelial damage to the gastric mucosa caused by those components.

Basically, Magaldrate creates an environment which promotes epithelial repair and cell regrowth.

Studies conducted on humans demonstrate that oral magaldrate intake is not followed by any significant absorption of aluminium or magnesium, and does not alter the calcium or phosphorus metabolism. Magaldrate only performs its action at gastrointestinal level, and has no systemic pharmacological effects or toxicity.

The therapeutic properties of magaldrate are not the same as those of other compounds based on aluminium and magnesium oxides, but derive from the specific ratio between the components, which is crucial in determining the buffer properties of the compound. In this respect, see the publication in *J Pharmacol Exp Ther.* 1992 December; 263(3): 1206-11 which demonstrates that compounds with different Al/Mg ratios have similar activities in vitro but different activities in vivo, where the aluminium ions tend to form complexes.

DESCRIPTION OF THE INVENTION

It has now been found that topical magaldrate exerts a regenerating and anti-inflammatory action on the damaged epidermis, e.g. in the case of ulcers, venous ulcers, superficial ulcers, wounds, burns, eczema, rashes, psoriasis, ulcers, venous ulcers, superficial ulcers, wounds, burns, eczema, rashes, psoriasis, cutaneous lesions, diabetic lesions, traumatic lesions, surgical wounds, abrasions, dermatitis, macerations, stoma skin complications, inflammatory and/or infective skin disorders.

The present invention therefore relates to topical compositions of magaldrate suitable for application to the skin and the nasal, vaginal and rectal mucous membranes.

Examples of suitable carriers include native collagen, particularly native collagen type i, ii and iii from any source such as equine, bovine, porcine or aviarian collagen, vegetal collagen, hydrolyzed collagen, synthetic collagen. collagen may be in lyophilised or gel form. hyaluronic acid or derivatives thereof such as sodium hyaluronate, in crystalline form or in solution, as well as alginates may be conveniently used as carriers for magaldrate.

The compositions according to the invention can be formulated in any form convenient for topical use, in particular cream, vaginal/rectal cream, lotion, dusting powder, gel, creamgel, foams, powders for spray doser, patches, gauzes, hydrofibers, hydrocolloids, hydrogel, alginates, sponges, tissues/tablets, adhesive or non adhesive-films.

Examples of preferred combinations of the above mentioned carriers and/or ingredients include:

Magaldrate+collagen;
Magaldrate+collagen+hyaluronic acid;
Magaldrate+collagen+hyaluronic acid+silver;
Magaldrate+collagen+hyaluronic acid+zinc;
Magaldrate+collagen+hyaluronic acid+silver+zinc;
Magaldrate+collagen+hyaluronic acid+zinc+alginates;
Magaldrate+collagen+hyaluronic acid+zinc+alginates+silver.

Magaldrate is present in the formulations in concentrations of between 0.1% and 30% by weight, and preferably between 1% and 15% in the case of the cream or lotion formulations, while for powders, magaldrate can be present in percentages of between 0.5% and 50% by weight, and preferably between 1% and 15%.

The properties of magaldrate can be supplemented by adding adjuvants, synergic and/or complementary substances such as vitamin E (tocopherols), vitamin A (retinol), vitamin C, alpha lipoic, carnosine, zinc compounds, zinc oxide, cysteine, flavonoids, carotenoids, phytosterols, aloe, ozonized oil, alginates, amikacin or other antibiotics/anti-septics, silver compounds (e.g. colloidal silver, nanocrystalline silver, silver nitrate, silver sulphadiazine, silver acetylmethionate, silver borosilicate, silver sulfate), iodine or iodine compounds, chlorhexidine or local anaesthetics (dibucaine, benzocaine or lidocaine).

For treatments of the mucous membranes, such as the vaginal mucosa, the product can be formulated as a vaginal pessary, ointment, suspension or cream. These preparations can be manufactured by known techniques, using conventional excipients.

For example, a fatty base, one or more emulsifying agents, an aqueous phase and one or more antimicrobial agents are generally used for the cream formulation. The following ingredients are used:

Fatty substance amounting to between 5% and 70% by weight, and preferably between 10% and 40%.

Emulsifying agent amounting to between 0% and 20% by weight, and preferably between 0.5% and 10%.

Water amounting to between 10% and 90% by weight, and preferably between 40% and 80%.

Thickening agent amounting to between 0% and 6% by weight, and preferably between 0% and 2%.

An antimicrobial preservative.

Chelating agents, antioxidants, and pharmaceutical form stabilisers.

"Fatty base" means a substance that is liquid or solid at ambient temperature which may be an aliphatic fatty acid ester, an aromatic acid ester, a triglyceride, a long-chain aliphatic alcohol, vaseline, lanolin or liquid paraffin.

The fatty substance used is not limited to a particular quantity but can vary, depending on the characteristics of the cream.

Anionic, cationic, non-ionic or amphoteric surfactants can be used as emulsifying agents. The non-ionic type is generally preferable because it is less irritating to the damaged skin; it may be the oxyethylenated, polyhydroxide or polymer type. The oxyethylenated type can be a derivative between an alcohol with a high molecular weight and a fatty acid, or an oxyethylenated derivative of a alkyl-phenol, an aliphatic amine, a polyvalent alcohol, etc.

The polyhydroxide type can include, for example, fatty acid monoesters of glycerin, a sorbitan ester of fatty acid, an amide between a fatty acid and ethanolamine, a monoester between a fatty acid and polyoxypropylene, a monoester between a fatty acid and polyoxyethylene glycerin, and so on. Said emulsifying agents can be used separately or mixed together.

The emulsifying agent used is not restricted to a particular quantity, but can vary according to the desired characteristics of the end product. Said quantity is usually between 1% and 20%, and preferably between 3% and 15%, by weight.

Conventional excipients are used for the lotion formulation; they basically comprise a fatty base, one or more emulsifying agents, an aqueous phase, and one or more antimicrobial agents. The following ingredients are used:

A liquid fatty substance amounting to between 1% and 40% by weight, and preferably between 5% and 20%.

Emulsifying agent amounting to between 0% and 20% by weight, and preferably between 0.5% and 5%.

Water amounting to between 0% and 90% by weight, and preferably between 50% and 80%.

A thickening agent amounting to between 0% and 6% by weight, and preferably between 0.05% and 2%.

An antimicrobial preservative.

Chelating agents, antioxidants, and pharmaceutical form stabilisers.

The dusting powder formulation is particularly indicated in cases involving formation of exudates, which are absorbed and agglomerated by the product, thus creating an effective barrier against external agents which often cause further complications.

Conventional excipients with a very fine particle size, generally <100 microns, are used to prepare the dusting powder.

The excipients act as diluents, promote the flowability of the powder mixture, and prevent it from caking.

The following ingredients are used:

An ingredient acting as a diluent amounting to between 30% and 99% by weight, and preferably between 75% and 95%.

Flowability promoter amounting to between 0% and 20% by weight, and preferably between 0.5% and 5%.

Chelating agents, antioxidants, and pharmaceutical form stabilisers.

The following examples illustrate the invention in greater detail.

Example No. 1

| Cream based on 5% magaldrate for topical use | |
|---|---|
| MAGALDRATE | 5.0 g |
| CRODAMOL SSE | 8.0 g |
| CITHROL GMS SE | 5.5 g |
| STEARIC ACID | 4.0 g |
| CRODA BASE | 3.0 g |
| CETOMACROGOL 1000 | 3.0 g |
| ISOPROPYL MYRISTATE | 2.5 g |
| ISOFOL 20 | 1.0 g |
| BUTYLHYDROXYANISOL | 0.05 g |
| BUTYLHYDROXYTOLUENE | 0.05 g |
| MIXTURE OF PARABENS | 0.3 g |
| DISODIUM EDTA | 0.1 g |
| SODIUM DEHYDROACETATE | 0.1 g |
| IMIDAZOLIDINYL UREA | 0.2 g |
| LACTIC ACID | q.s. to pH 5.5 |
| PURIFIED WATER | q.s. to 100 g |

Example No. 2

| Cream based on 2.5% magaldrate + amikacin for topical use | |
|---|---|
| MAGALDRATE | 2.5 g |
| AMIKACIN | 2.5 g |
| SORBITAN MONOSTEARATE | 1.5 g |
| ISOPROPYL MYRISTATE | 5.0 g |
| STEARYL ALCOHOL | 6.0 g |
| POLYSORBATE 60 | 2.5 g |
| PROPYLENE GLYCOL | 20.0 g |
| BENZOIC ACID | 0.2 g |
| CETYL ALCOHOL | 5.0 g |
| PURIFIED WATER | q.s. to 100 g |

Example No. 3

| Cream based on 2% magaldrate + vit. E for topical use | |
|---|---|
| MAGALDRATE | 2.0 g |
| VITAMIN E ACETATE | 5.0 g |
| POLYOXYETHYLENEGLYCOL PALMITATE-STEARATE | 9.0 g |

-continued

| Cream based on 2% magaldrate + vit. E for topical use | |
|---|---|
| POLYOXYETHYLATED GLYCERIDES OF SATURATED FATTY ACIDS | 5.8 g |
| METHYL PARABEN | 0.135 g |
| PROPYL PARABEN | 0.015 g |
| PURIFIED WATER | q.s. to 100 g |

Example No. 4

| Cream based on 10% magaldrate for vaginal use | |
|---|---|
| MAGALDRATE | 10.0 g |
| GLYCERYL STEARATE | 5.5 g |
| STEARIC ACID | 4.0 g |
| CETOMACROGOL 1000 | 3.0 g |
| ISOPROPYL MYRISTATE | 2.5 g |
| 2-OCTYLDODECANOL | 1.0 g |
| BUTYLHYDROXYANISOL | 0.05 g |
| BUTYLHYDROXYTOLUENE | 0.05 g |
| DISODIUM EDTA | 0.1 g |
| METHYL PARABEN | 0.200 g |
| PROPYL PARABEN | 0.025 g |
| SODIUM DEHYDROACETATE | 0.1 g |
| IMIDAZOLIDINYL UREA | 0.2 g |
| LACTIC ACID | q.s. to pH 5.5 |
| PURIFIED WATER | q.s. to 100 g |

As regards the preparation process, Magaldrate and the other ingredients, apart from the fatty components, are dissolved or dispersed in the hot aqueous phase (70-80° C.). The fatty substances, heated to 65-75° C., are then added to the aqueous phase and subjected to suitable stirring (mixer).

Example No. 5

| Lotion based on 7.5% magaldrate | |
|---|---|
| MAGALDRATE | 7.5 g |
| GLYCERIN | 5.0 g |
| AVICEL R GEL | 2.0 g |
| CARBOXYMETHYLCELLULOSE | 2.5 g |
| BENZALKONIUM CHLORIDE | 0.50 g |
| PURIFIED WATER | q.s. to 100 g |

The preparation of the pharmaceutical lotion is similar to that of the cream.

Example No. 6

| Dusting powder based on 5% magaldrate and 2% zinc oxide | |
|---|---|
| MAGALDRATE | 5.0 g |
| ZINC OXIDE | 2.0 g |
| COLLOIDAL SILICON DIOXIDE | 5.0 g |
| CORN STARCH | 20.0 g |
| TALC | 68.0 g |

Preparation

The preparation involves simply mixing the ingredients. However, this operation must be conducted under conditions that guarantee the sterility of the product.

Example No. 7

| Cream based on magaldrate 1% and collagene 5% | |
|---|---|
| COMPONENTS: | % (P/P) |
| EMULGIN BA 25 | 3 |
| LANETTE O OR | 6 |
| LANETTE 22 | 4 |
| EMULGIN SG | 0.5 |
| MYRITOL 331 | 1 |
| CETIOL CC | 8 |
| DIMETICONE | 0.5 |
| BHA | 0.05 |
| BHT | 0.05 |
| PARABENS MNIXTURE | 0.3 |
| IMIDAZOLIDINYL UREA | 0.2 |
| DISODIUM EDTA | 0.1 |
| SODIUM DEHYDROACETATE | 0.1 |
| NATIVE COLLAGEN TYPE I 1% GEL | 5 |
| MAGALDRATE | 1 |
| LACTIC ACID | q.s. to PH = 5.5 |
| WATER | q.s. to 100% |

Example No. 8

| Cream based on magaldrate 3% and collagen 5% | |
|---|---|
| COMPONENTS: | % (P/P) |
| EMULGIN BA 25 | 3 |
| LANETTE O OR | 6 |
| LANETTE 22 | 4 |
| EMULGIN SG | 0.5 |
| MYRITOL 331 | 1 |
| CETIOL CC | 8 |
| DIMETICONE | 0.5 |
| BHA | 0.05 |
| BHT | 0.05 |
| PARABENS MNIXTURE | 0.3 |
| IMIDAZOLIDINYL UREA | 0.2 |
| DISODIUM EDTA | 0.1 |
| SODIUM DEHYDROACETATE | 0.1 |
| NATIVE COLLAGEN TYPE I 1% GEL | 5 |
| MAGALDRATE | 3 |
| LACTIC ACID | q.s. to PH = 5.5 |
| WATER | q.s. to 100% |

Example No. 9

| Cream based on magaldrate 5% and collagene 5% | |
|---|---|
| COMPONENTS: | % (P/P) |
| EMULGIN BA 25 | 3 |
| LANETTE O OR COGNIS | 6 |
| LANETTE 22 | 4 |
| EMULGIN SG | 0.5 |
| MYRITOL 331 | 1 |
| CETIOL CC | 8 |
| DIMETICONE | 0.5 |

-continued

Cream based on magaldrate 5% and collagene 5%

| COMPONENTS: | % (P/P) |
| --- | --- |
| BHA | 0.05 |
| BHT | 0.05 |
| PARABENS MNIXTURE | 0.3 |
| IMIDAZOLIDINYL UREA | 0.2 |
| DISODIUM EDTAAGRAR | 0.1 |
| SODIUM DEHYDROACETATE AGRAR | 0.1 |
| NATIVE COLLAGEN TYPE I 1% GEL | 5 |
| MAGALDRATE | 5 |
| LACTIC ACID | q.s. to PH = 5.5 |
| WATER | q.s. to 100% |

Preparation

The lipohilic phase is heated to 70-75° C., stirring with a mixer to obtain melting/homegeneization of the components. Part of water is added with stirring, keeping the above temperature. Temperature is then lowered to T<40° C., the hydrophilic components are dissolved/dispersed the powders in water, then added with stirring to complete homogeization. Finally pH is adjusted with lactic acid.

The invention claimed is:

1. A method of treatment of irritative and inflammatory states of the skin and mucosa associated with non-infective conditions selected from superficial ulcers, wounds, burns, eczema, rashes, and psoriasis, comprising the topical administration of a therapeutically effective amount of a magaldrate composition comprising of 0.1% to 30% by weight magaldrate to a portion of the skin or mucosa of a subject that is in need thereof.

2. The method of claim 1 wherein the magaldrate is mixed with suitable vehicles and excipients.

3. The method of claim 1 wherein the magaldrate is in the form of a cream, lotion, dusting powder, pessary or suppository, gel, creamgel, foams, powders for spray doser, patches, gauzes, hydrofibers, hydrocolloids, hydrogel, alginates, sponges, tissues, tablets, adhesive or non adhesive-films.

4. The method of claim 1 wherein the magaldrate is in the composition containing one or more of vitamin E, vitamin A, vitamin C, zinc compounds, zinc oxide, cysteine, silver compounds, alpha-lipoic acid, camosine, ozonized oil, alginates, phytosterols, flavonoids, carotenoids, aloe, Chitosan, iodine and iodine compounds, chlorhexidine, antibiotics, anti-septics, and local anaesthetics.

* * * * *